US011439557B2

(12) United States Patent
Lehman et al.

(10) Patent No.: US 11,439,557 B2
(45) Date of Patent: Sep. 13, 2022

(54) MODULAR SURGICAL SYSTEM

(71) Applicant: Allen Medical Systems, Inc., Batesville, IN (US)

(72) Inventors: Vincent Lehman, Groton, MA (US); Alexander E. Rojas, Waltham, MA (US); Michael C. Pierce, Harvard, MA (US)

(73) Assignee: Allen Medical Systems, Inc., Batesville, IN (US)

(*) Notice: Subject to any disclaimer, the term of this patent is extended or adjusted under 35 U.S.C. 154(b) by 523 days.

(21) Appl. No.: 16/411,301

(22) Filed: May 14, 2019

(65) Prior Publication Data

US 2019/0374420 A1    Dec. 12, 2019

Related U.S. Application Data

(60) Provisional application No. 62/681,296, filed on Jun. 6, 2018.

(51) Int. Cl.
| A61G 13/10 | (2006.01) |
| A61G 13/00 | (2006.01) |
| A61G 13/12 | (2006.01) |
| A61B 17/00 | (2006.01) |

(52) U.S. Cl.
CPC ....... *A61G 13/105* (2013.01); *A61G 13/0054* (2016.11); *A61G 13/1285* (2013.01); *A61B 2017/00486* (2013.01)

(58) Field of Classification Search
CPC .............. A61G 13/105; A61G 13/0054; A61G 13/1285; A61G 13/04; A61G 13/104; A61G 13/06; A61G 7/05; A61B 2017/00486; A47C 21/003
USPC .......................................................... 5/626
See application file for complete search history.

(56) References Cited

U.S. PATENT DOCUMENTS

| 2,872,259 | A |   | 2/1959  | Thorpe |
| 3,046,072 | A |   | 7/1962  | Douglass, Jr. et al. |
| 4,195,829 | A |   | 4/1980  | Reser |
| 4,589,642 | A | * | 5/1986  | Schnelle ................ A61G 13/02 |
|           |   |   |         | 5/608 |
| 4,872,656 | A |   | 10/1989 | Brendgord et al. |

(Continued)

FOREIGN PATENT DOCUMENTS

| DE | 102009047869 A1 | 3/2011 |
| EP |      3124000 A1 | 2/2017 |
| GB |      2405789 A  | 3/2005 |

OTHER PUBLICATIONS

Extended European Search Report for Application No. 19178217.6, dated Oct. 16, 2019, 8 pages.

(Continued)

*Primary Examiner* — David R Hare
*Assistant Examiner* — Luke Hall
(74) *Attorney, Agent, or Firm* — Barnes & Thornburg LLP

(57) ABSTRACT

A modular surgical system includes a base and a column extending from the base. An adaptor is positioned at a top of the column. An elevation assembly is provided to adjust a height of the adaptor. A control system is positioned in at least one of the base or the column. The control system is configured to communicate with remote devices. The control system is further configured to control the elevation assembly.

22 Claims, 4 Drawing Sheets

(56) References Cited

U.S. PATENT DOCUMENTS

| | | | |
|---|---|---|---|
| 5,918,331 A * | 7/1999 | Hall | A61G 1/00 5/503.1 |
| 5,975,081 A * | 11/1999 | Hood | A61G 1/04 128/845 |
| 6,155,260 A * | 12/2000 | Lavin | A61G 1/04 128/845 |
| 6,295,671 B1 | 10/2001 | Reesby et al. | |
| 6,484,334 B1 * | 11/2002 | Borders | A61G 13/08 5/713 |
| 6,523,197 B2 | 2/2003 | Zitzmann | |
| 7,152,261 B2 | 12/2006 | Jackson | |
| 7,520,008 B2 | 4/2009 | Wong et al. | |
| 8,353,071 B2 | 1/2013 | Turner et al. | |
| 9,072,646 B2 | 7/2015 | Skripps et al. | |
| 9,358,170 B2 | 6/2016 | Jackson | |
| 9,402,775 B2 | 8/2016 | Jackson et al. | |
| 9,468,576 B2 | 10/2016 | Jackson | |
| 9,498,397 B2 | 11/2016 | Hight et al. | |
| 9,549,863 B2 | 1/2017 | Jackson et al. | |
| 9,757,299 B2 | 9/2017 | Hight et al. | |
| 10,368,949 B2 * | 8/2019 | Giulianotti | A61B 34/30 |
| 2002/0170116 A1 * | 11/2002 | Borders | A61G 12/002 5/618 |
| 2004/0216232 A1 | 11/2004 | Bradcovich | |
| 2005/0166324 A1 * | 8/2005 | Dixon | A61G 7/0509 5/616 |
| 2006/0185091 A1 | 8/2006 | Jackson | |
| 2010/0031443 A1 * | 2/2010 | Georgiev | A61B 5/055 5/601 |
| 2010/0074681 A1 * | 3/2010 | Jamalzadeh | A61G 12/004 439/211 |
| 2010/0187379 A1 | 7/2010 | Kragh et al. | |
| 2013/0269710 A1 * | 10/2013 | Hight | A61G 13/02 128/845 |
| 2014/0068861 A1 | 3/2014 | Jackson et al. | |
| 2014/0109316 A1 | 4/2014 | Jackson | |
| 2014/0130259 A1 * | 5/2014 | Eisenmann | A61G 7/018 254/2 R |
| 2016/0000620 A1 * | 1/2016 | Koch | A61G 7/005 5/608 |
| 2016/0000626 A1 * | 1/2016 | Jackson | A61G 13/04 5/608 |
| 2016/0128880 A1 * | 5/2016 | Blickensderfer | A61G 1/0262 296/20 |
| 2016/0331614 A1 * | 11/2016 | Furman | A61G 7/0506 |
| 2017/0027797 A1 * | 2/2017 | Dolliver | A61G 13/122 |
| 2017/0119610 A1 * | 5/2017 | Christensen | A61G 13/105 |
| 2018/0164872 A1 * | 6/2018 | Graf | G06F 1/3212 |
| 2018/0221098 A1 * | 8/2018 | Forsyth | A61B 17/7082 |
| 2018/0289575 A1 * | 10/2018 | Hiratsuka | A61G 13/101 |
| 2018/0344559 A1 * | 12/2018 | Hoel | A61G 13/1285 |
| 2019/0183251 A1 * | 6/2019 | Niederkofler | A61G 7/0527 |
| 2019/0374417 A1 * | 12/2019 | Hiratsuka | A61G 13/06 |

OTHER PUBLICATIONS

Extended European Search Report for Application No. 21197543.8, dated Jan. 28, 2022, 8 pages.

* cited by examiner

MODULAR SURGICAL SYSTEM

CROSS REFERENCE TO RELATED APPLICATIONS

This application claims priority under 35 U.S.C. § 119(e) to U.S. Provisional Patent Application Ser. No. 62/681,296, filed Jun. 6, 2018, which is expressly incorporated by reference herein.

BACKGROUND

The present disclosure relates to surgical systems, and more particularly, to a modular surgical system.

Generally, spine tables have two columns and require a cross tube between the columns to provide stability to the columns. Additionally, power and communication between the columns may be provided through the cross tube. Because of the cross-tube, spine tables typically take up a significant amount of space. It is also difficult sometimes to position the table in certain operating rooms, e.g. smaller operating rooms. Moreover, the cross tube prevents any devices from being passed under the table during a procedure.

Storage is also a problem that many health care facilities face. A two column spine table is often difficult to store because the columns cannot be separated and the cross tube requires the table to remain at full length. Because most spine tables are charged during storage, the inability to reduce the size of the table mandates that a storage room must have both the space for the table and access to an outlet. This combination of features may be difficult to find in some health care facilities.

SUMMARY

The present disclosure includes one or more of the features recited in the appended claims and/or the following features which, alone or in any combination, may comprise patentable subject matter.

According to an aspect of the disclosed embodiments, a modular surgical system may include a base. A column may extend from the base. An adaptor may be positioned at a top of the column. The adaptor may have a movement system configured to couple to a table top. A control system may be positioned in at least one of the base or the column. The control system may be configured to communicate with remote devices. The control system may be further configured to control the movement system of the adaptor to move the table top.

It may be contemplated that the table top may be coupled to the adaptor of the modular surgical system and an adaptor of a second modular surgical system so that the table top extends between the column of the modular surgical system and a column of the second modular surgical system. The control system of the modular surgical system may communicate with a control system of the second modular surgical system. The control system of the modular surgical system may communicate with a control system of the second modular surgical system to at least one of adjust a height of the table top or tilt the table top. At least one of the control system of the modular surgical system and the control system of the second modular surgical system may operate as a primary control system. The primary control system may communicate with a remote device. The table top may be sized to an operating room.

In some embodiments, the control system may identify the table top coupled to the adaptor. The medical system may include at least one of a spine table top, an orthopaedic table top, a cervical table top, or a standard operating table top.

Optionally, a battery may be positioned in the base. An outlet may be provided to charge the battery. An outlet may be provided to couple the battery to a battery of a second modular surgical system.

Additionally or alternatively, casters may be coupled to the base so that the modular surgical system is portable. The modular surgical system may be portable.

According to another aspect of the disclosed embodiments, a modular surgical system may include a portable column having an adaptor. A control system may be configured to communicate with remote devices. The control system may be further configured to control the adaptor. The adaptor may be configured to couple the column to a table top. The control system may be configured to control the table top coupled to the adaptor.

In some embodiments, the table top may be coupled to the adaptor of the modular surgical system and an adaptor of a second modular surgical system so that the table top extends between the column of the modular surgical system and a column of the second modular surgical system. The control system of the modular surgical system may communicate with a control system of the second modular surgical system. The control system of the modular surgical system may communicate with a control system of the second modular surgical system to at least one of adjust a height of the table top or tilt the table top. At least one of the control system of the modular surgical system and the control system of the second modular surgical system may operate as a primary control system. The primary control system may communicate with a remote device. The table top may be sized to an operating room.

It may be desired that the control system identify the table top coupled to the adaptor. The table may include at least one of a spine table top, an orthopaedic table top, a cervical table top, or a standard operating table top.

Optionally, a battery may be provided. An outlet may be provided to charge the battery. An outlet may be provided to couple the battery to a battery of a second modular surgical system. Casters may be coupled to the column.

According to yet another aspect of the disclosed embodiments, a modular surgical system may include a first column having a first control system. A first adaptor may be positioned at a top of the first column. A second column may include a second control system. A second adaptor may be positioned at a top of the second column. A table top may be coupled to the first adaptor and the second adaptor and extend between the first column and the second column. The first control system may communicate with the second control system to at least one of adjust a height of the table top and tilt the table top.

In some embodiments, at least one of the first control system and the second control system may operate as a primary control system. The primary control system may communicate with a remote device. The table top may be sized to an operating room.

Optionally, a first battery may be positioned in the first column and a second battery may be positioned in the second column. A first outlet may be provided to charge the first battery. An outlet may be provided to couple the first battery to the second battery. First casters may be coupled to the first column and second casters may be coupled to the second column. The modular surgical system may be portable.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
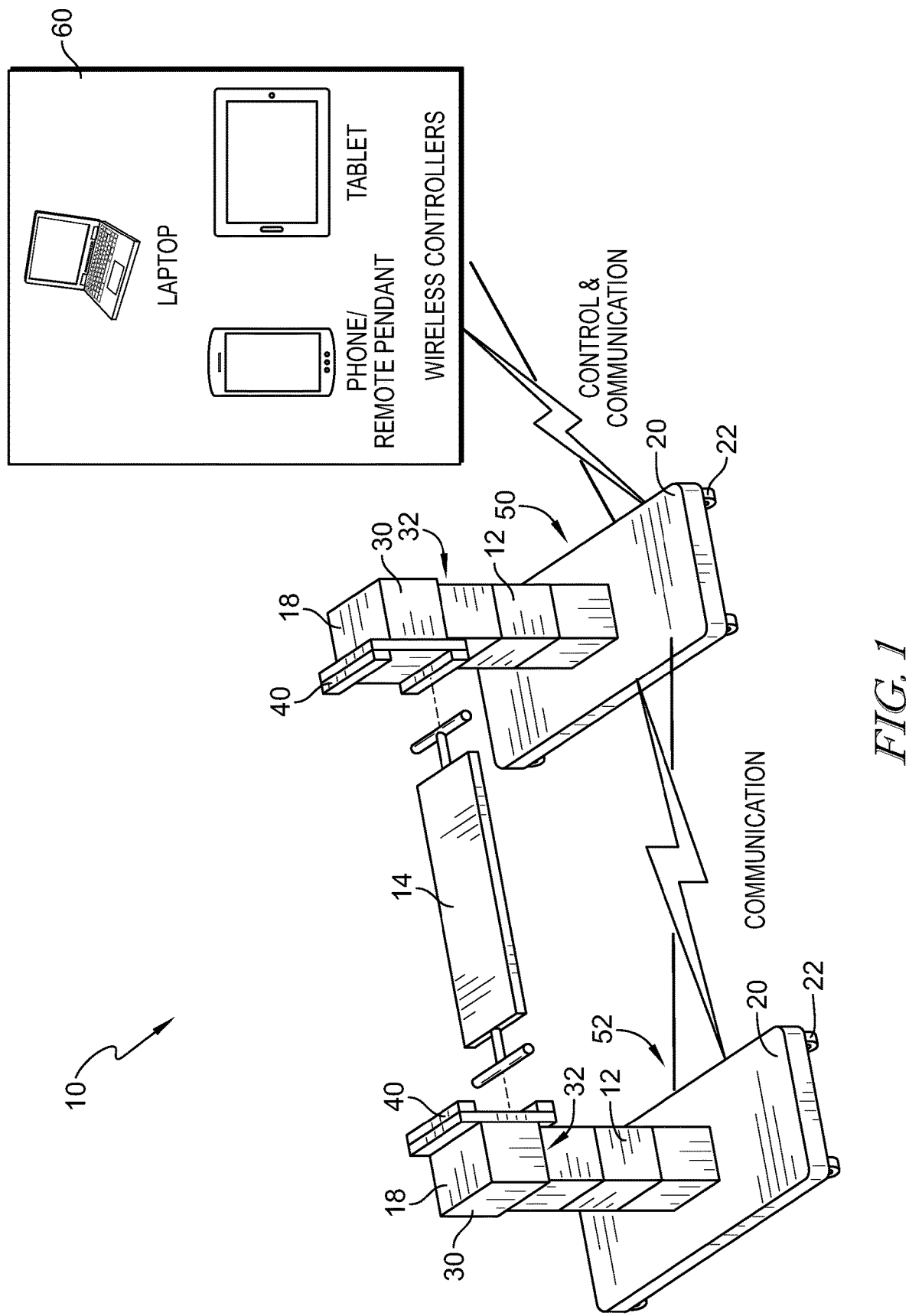
FIG. 1 is a side perspective view of a surgical table assembly in accordance with an embodiment.

Referring to FIG. 1 a surgical table assembly 10 includes a pair of modular components 18 having base columns 12 and an adaptor 30. A surgical table top 14 is coupled to the adaptors 30 and extends between the columns 12. The columns 12 are telescopic and adjustable in height. Each column 12 includes a base 20 having casters 22 to enable movement of the column 12. Notably, a cross-bar does not extend between the columns 12. Accordingly, other components may be rolled under the table top 14 during a procedure. Additionally, the table top 14 may be removed from the columns 12 so that the columns 12 can be stored side by side. In the illustrative embodiments, the surgical table top 14 is a spine table. In some embodiments, the surgical table top 14 may be an orthopaedic table top, a cervical table top, a standard operating table top, or the like. In some embodiments the columns 12 are adapted to couple to any size table top 14 to preserve space in an operating room.

The adaptor 30 is positioned at the top 32 of each column 12. The adaptor 30 is adaptable to the table top 14 being coupled to the columns. For example, as illustrated, the adaptor 30 includes an elevation assembly 40 to adjust the height of the spine table top 14. The elevation assembly 40 may be an assembly as described in U.S. Patent Ser. No. 62/636,563, filed Feb. 28, 2018, and titled "PATIENT SUPPORT AND METHODS THEREOF," which is hereby incorporated by reference in its entirety. The assembly 40 may also rotate the spine table top 14. In the illustrated embodiment, the assembly 40 is specific to the spine table top 14. In other embodiments, the adaptor 30 may include an assembly 40 that is specific to another type of table. For example, the assembly 40 may include components that are specific to a standard operating room table. Although many configurations of tables 14 may be attached to the columns 12, the present disclosure will be described with respect to a spine table top 14.

A first modular component 50 is configured to communicate with a second modular component 52. That is, the modular component 50 may operate as the primary modular component or primary control system. The first modular component 50 is configured to communicate wirelessly with the second modular component 52 so that the modular component 50 controls the adaptor 30 of each modular component 50, 52. For example, the modular component 50 may be operated to tilt the assembly 40 to tilt the table top 14. In such an embodiment, the modular component 50 communicates with the modular component 52 to instruct the modular component 52 to also tilt its respective assembly 40. In this way, both assemblies 40 rotate in unison to prevent unwanted torsional forces or breakage of the table top 14. In the illustrative embodiment, the first modular component 50, acting as the primary modular component, also communicates with a remote device 60, e.g. a smart phone, a tablet, a remote computer, or the like. Accordingly, the modular component 50, 52 can be controlled with the remote device 60.

Figure 2:
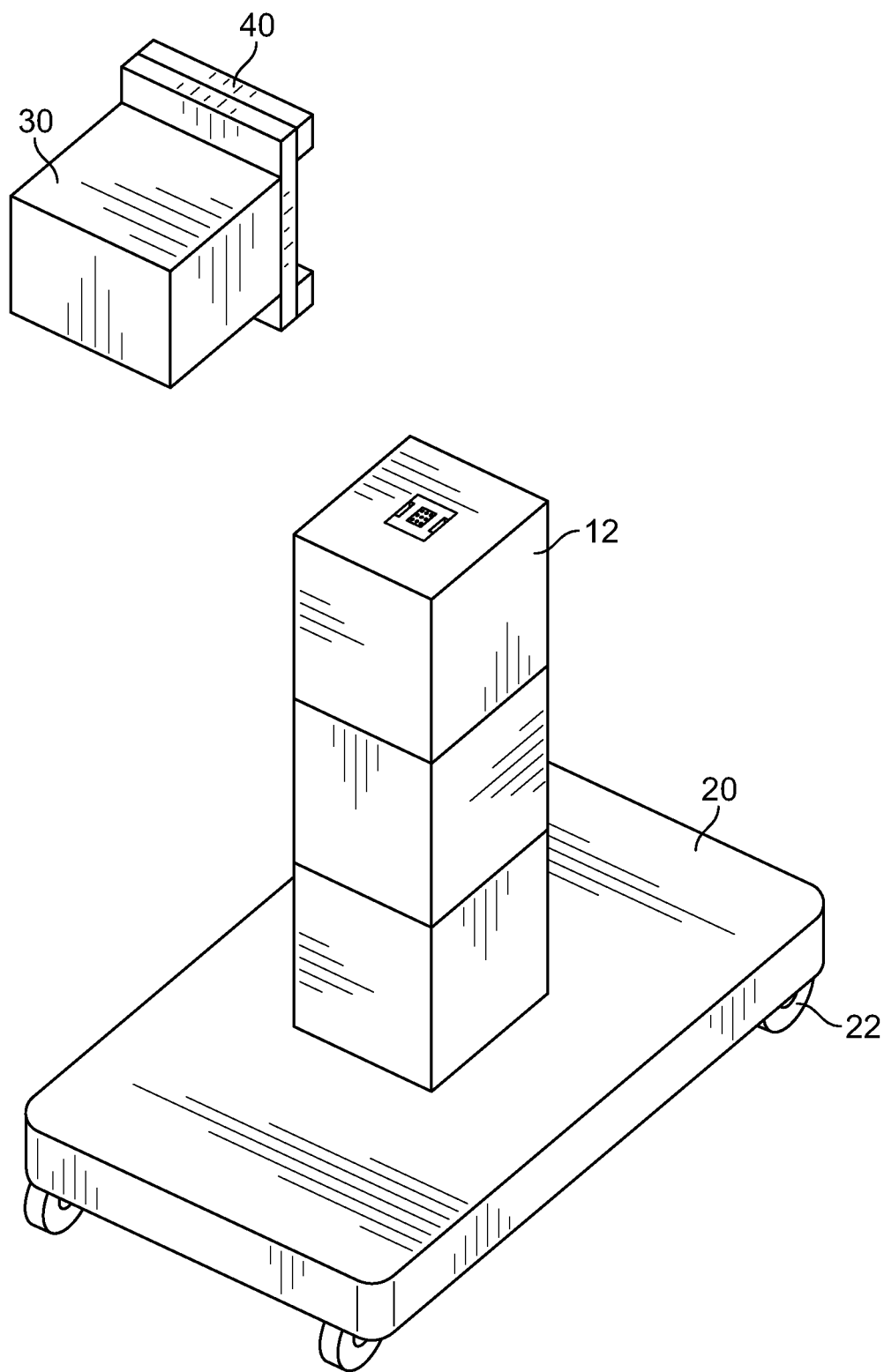
FIG. 2 is a side perspective view of a modular component of the surgical table assembly.
Figure 3:
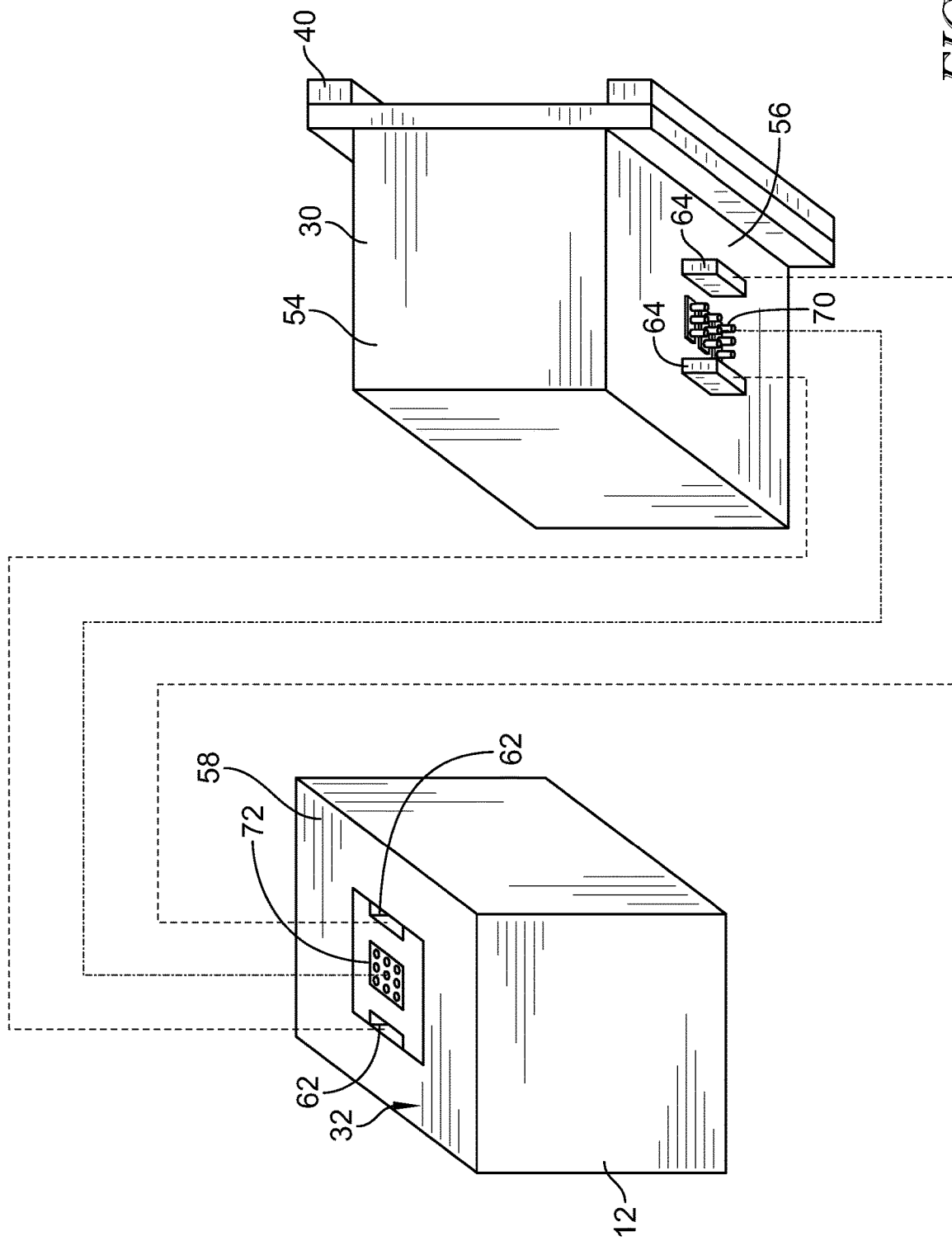
FIG. 3 is an exploded view of portions of the modular component of the surgical table assembly showing the adaptor removed from a top of the column.

Referring to FIG. 2, the adaptor 30 is detachable from the column 12. The adaptor 30 is specific to the table top 14, e.g. a spine adaptor for a spine table top 14. When the table top 14 is changed, the adaptor 30 is removed from the column 12. For example, when the table top 14 is changed to a standard operating room table, the adaptor 30 for the standard operating room table is attached to the column 12. As seen in FIG. 3, the adaptor 30 includes a housing 54 having a bottom surface 56. The bottom surface 56 is configured to position on a top surface 58 of the column 12. The top surface 58 of the column 12 includes openings 62 to receive flanges 64 extending from the bottom surface 56 of the adaptor 30. The flanges 64 lock into the openings 62 to secure the adaptor 30 to the column 12. In other embodiments, any coupling mechanism may be utilized to secure the adaptor 30 to the column 12.

The adaptor 30 also includes a plurality of electrical pins 70 that extend from the bottom surface 56 of the adaptor 30. The electrical pins 70 are configured to be received in an outlet 72 on the top surface 58 of the column 12 to transfer electrical signals from the column 12 to the adaptor 30. As described below, the adaptor 30 includes the elevation assembly 40. By electrically coupling the column 12 to the elevation assembly 40, the column 12 may be utilized to control the elevation assembly 40. In some embodiments, any plug and socket configuration may be utilized to electrically couple the column 12 to the adaptor 30.

Figure 4:
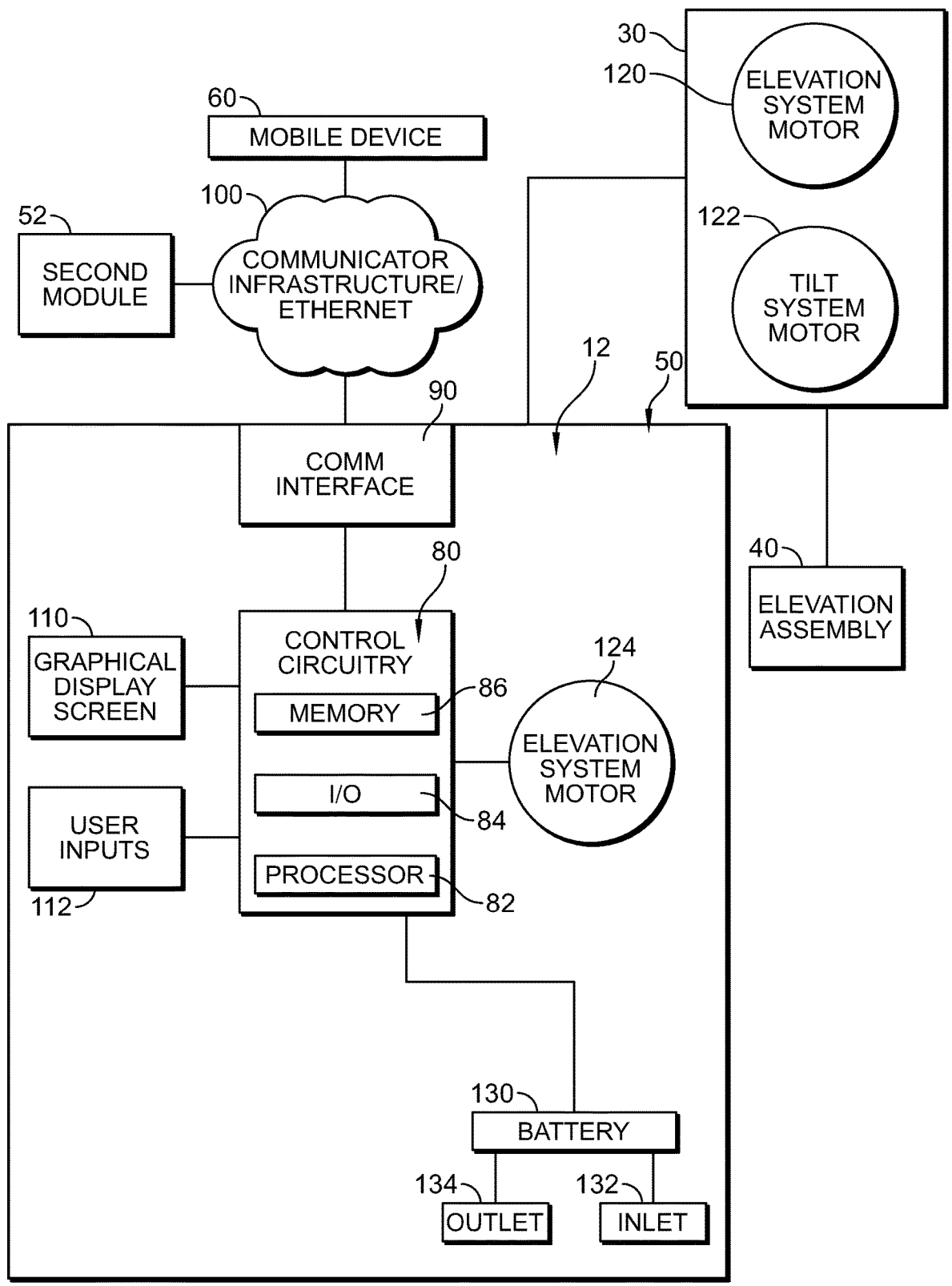
FIG. 4 is a schematic view of a control circuitry of the modular component of the surgical table assembly.

Referring to FIG. 4, the modular components 18 include control circuitry 80 that is positioned in the column 12 or the base 20. The control circuitry 80 illustratively includes a processor 82, an input/output subsystem 84, a memory 86, and a communication subsystem 90, and/or other components and devices commonly found in a server computer or similar computing device. Of course, the control circuitry 80 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 86, or portions thereof, may be incorporated in the processor 82 in some embodiments.

The processor 82 may be embodied as any type of processor capable of performing the functions described herein. The processor 82 may be embodied as a single or multi-core processor(s), digital signal processor, microcontroller, or other processor or processing/controlling circuit. Similarly, the memory 86 may be embodied as any type of volatile or non-volatile memory or data storage capable of performing the functions described herein. In operation, the memory 86 may store various data and software used during operation of the control circuitry 80, such as operating systems, applications, programs, libraries, and drivers. The memory 86 is communicatively coupled to the processor 82 via the I/O subsystem 84, which may be embodied as circuitry and/or components to facilitate input/output operations with the processor 82, the memory 86, and other components of the control circuitry 80. For example, the I/O subsystem 84 may be embodied as, or otherwise include, memory controller hubs, input/output control hubs, platform controller hubs, integrated control circuitry, firmware devices, communication links (i.e., point-to-point links, bus links, wires, cables, light guides, printed circuit board traces, etc.) and/or other components and subsystems to facilitate the input/output operations. In some embodiments, the I/O subsystem 84 may form a portion of a system-on-a-chip (SoC) and be incorporated, along with the processor 82, the memory 86, and other components of the control circuitry 80, on a single integrated circuit chip.

The communication subsystem 90 is configured to wirelessly communicate over a communication infrastructure/Ethernet 100. Over the Ethernet 100, the control circuitry 80 communicates with the second modular component 52. As such, the control circuitry 80 of the first modular component 50 is utilized to control the second modular component 50. The communication subsystem 90 also communicates with the remote device 60 also communicates with the control circuitry 80 via the Ethernet 100. In an illustrative embodiment, the remote device 60 may communicate commands to the first modular component 50, which commands are then relayed to the second modular component 52. As such, from the remote device 60, both the first modular component 50 and the second modular component 52 can be operated to work in unison to move the table top 14. Additionally, a graphical user interface 110 and user inputs 112 are provided on each modular component 18. Using the graphical user interface 110 and the user inputs 112, both modular components 18 may be controlled from a single modular component 18, e.g. first modular component 50.

In the illustrative embodiment, the modular component 18 includes an elevation system motor 124 to adjust a height of the column 12. The modular component 18 is also electrically coupled to the adaptor 30 through the electrical pins 70 and the outlet 72. The adaptor includes an elevation system motor 120 and a tilt system motor 122. The elevation system motor 120 and the tilt system motor 122 are coupled to the elevation assembly 40. Each motor 120, 122 is electrically coupled to the control circuitry 80 so that the control circuitry 80 controls each motor 120, 122. In the illustrative embodiment, a user enters commands for the elevation assembly 40 into either the remote device 60 or the graphical user interface 110. The control circuitry 80 of the first modular component 50 then relays the command to the control circuitry of the second modular component 52 so that the first modular component 50 and the second modular component 52 act is unison to control the motors 120, 122. The motors 120, 122 of each modular component 18 operate to raise or lower and to tilt the table top 14.

The modular component 18 also includes a battery 130 that is recharged when the modular component 18 is not in use. A pair of modular components 18 can be stored and charged side by side at a healthcare facility. The first modular component 50 is plugged into a wall outlet via an inlet 132. The second modular component 52 can be likewise plugged into a wall outlet via the inlet 132. Alternatively, a plug (not shown) may be extended between an outlet 134 of the first modular component 50 and the inlet 132 of the second modular component 52. As such, only the first modular component 50 is plugged into a wall outlet, and the second modular component 52 is charged off of the first modular component 50.

Typical two-column spine tables include a cross tube to provide stability, power and communications. The disclosed embodiments move the stability, power and communications of the table into two separate mobile systems. The disclosed embodiments allow the user to install a support top of any desired length to accommodate operating rooms with spatial limitations, as in the international markets. The disclosed embodiments allow the user to slide under table equipment under the table without concern of contact with a cross tube as in traditional two-column tables.

With storage space becoming a commodity within an operating room, the disclosed embodiments reduce the space required to store a spine surgery table. The two mobile systems can be stored adjacent to each other and charged on a single AC outlet with a jumper between the two mobile systems.

The disclosed embodiments can also be tailored for alternative uses other than spine surgery such as integration with measurement and diagnostic equipment requiring portability and height adjustability.

Although this disclosure refers to specific embodiments, it will be understood by those skilled in the art that various changes in form and detail may be made without departing from the subject matter set forth in the accompanying claims.

The invention claimed is:

1. A modular surgical system comprising:
a base,
a column extending from the base,
an electrical outlet positioned in a top surface of the column,
a plurality of adaptors, wherein each of the plurality of adaptors corresponds to a type of table top, wherein each of the plurality of adaptors is configured to position on the top surface of the column, wherein each of the plurality of adaptors includes an electrical connection configured to be inserted into the electrical outlet of the column with the respective adaptor positioned on the top surface of the column so that each of the plurality of adaptors is interchangeable on the column and can electrically communicate with the column, wherein each of the plurality of adaptors has a movement system configured to couple to the corresponding type of table top, and
a control system positioned in at least one of the base or the column, the control system configured to communicate with remote devices, the control system further configured to control the movement system of the respective adaptor of the plurality of adaptors positioned on the top surface of the column to move the table top.

2. The modular surgical system of claim 1, wherein the table top is coupled to a first adaptor of the modular surgical system and second adaptor of a second modular surgical system so that the table top extends between the column of the modular surgical system and a column of the second modular surgical system.

3. The modular surgical system of claim 2, wherein the control system of the modular surgical system is configured to communicate with a control system of the second modular surgical system.

4. The modular surgical system of claim 3, wherein the control system of the modular surgical system is configured to communicate with a control system of the second modular surgical system to either adjust a height of the table top or tilt the table top or both.

5. The modular surgical system of claim 3, wherein at least one of the control system of the modular surgical system and the control system of the second modular surgical system operates as a primary control system.

6. The modular surgical system of claim 5, wherein the primary control system communicates with the remote devices.

7. The modular surgical system of claim 1, wherein the control system identifies the type of table top coupled to the respective adaptor of the plurality of adaptors.

8. The modular surgical system of claim 1, wherein the type of table top comprises at least one of a spine table top, an orthopaedic table top, a cervical table top, or a standard operating table top.

9. The modular surgical system of claim 1, further comprising a battery positioned in the base.

10. The modular surgical system of claim 9, further comprising a power outlet to charge the battery.

11. The modular surgical system of claim 9, further comprising a power outlet to couple the battery to a battery of a second modular surgical system.

12. The modular surgical system of claim 1, further comprising casters coupled to the base so that the modular surgical system is portable.

13. The modular surgical system of claim 1, wherein the modular surgical system is portable.

14. A modular surgical system comprising:
a first column having a first control system,
a first electrical outlet positioned in a top surface of the first column,
a second column having a second control system,
a second electrical outlet positioned in a top surface of the second column,
a plurality of adaptors that are interchangeable on the first column and the second column,
wherein a first adaptor of the plurality of adaptors is positioned at a top of the first column, wherein the first adaptor includes an electrical connection configured to be inserted into the first electrical outlet of the first column with the first adaptor positioned on the top surface of the first column so that the first adaptor can electrically communicate with the first column,
wherein a second adaptor of the plurality of adaptors is positioned at a top of the second column, wherein the second adaptor includes an electrical connection configured to be inserted into the second electrical outlet of the second column with the second adaptor positioned on the top surface of the second column so that the second adaptor can electrically communicate with the second column, and
wherein the first adaptor and the second adaptor and correspond to a type of table top that extends between the first column and the second column, wherein the first adaptor is removable from the first column and the second adaptor is removable from the second column,
wherein the first control system is configured to communicate with the second control system to either adjust a height of the table top or tilt the table top or both.

15. The modular surgical system of claim 14, wherein at least one of the first control system and the second control system operates as a primary control system.

16. The modular surgical system of claim 15, wherein the primary control system communicates with a remote device.

17. The modular surgical system of claim 14, further comprising a first battery positioned in the first column and a second battery positioned in the second column.

18. The modular surgical system of claim 17, further comprising a first power outlet to charge the first battery.

19. The modular surgical system of claim 18, further comprising a second power outlet to couple the first battery to the second battery.

20. The modular surgical system of claim 14, further comprising first casters coupled to the first column and second casters coupled to the second column.

21. The modular surgical system of claim 14, wherein the modular surgical system is portable.

22. The modular surgical system of claim 14, wherein the type of table top comprises at least one of a spine table top, an orthopaedic table top, a cervical table top, or a standard operating table top.

* * * * *

UNITED STATES PATENT AND TRADEMARK OFFICE
CERTIFICATE OF CORRECTION

| | | |
|---|---|---|
| PATENT NO. | : 11,439,557 B2 | Page 1 of 1 |
| APPLICATION NO. | : 16/411301 | |
| DATED | : September 13, 2022 | |
| INVENTOR(S) | : Lehman et al. | |

It is certified that error appears in the above-identified patent and that said Letters Patent is hereby corrected as shown below:

In the Claims

In Column 8, Line 11, Claim 14, delete "second adaptor and" and insert -- second adaptor --.

Signed and Sealed this
Twenty-ninth Day of November, 2022

*Katherine Kelly Vidal*

Katherine Kelly Vidal
*Director of the United States Patent and Trademark Office*